(12) United States Patent
Sawhney et al.

(10) Patent No.: US 6,703,047 B2
(45) Date of Patent: Mar. 9, 2004

(54) DEHYDRATED HYDROGEL PRECURSOR-BASED, TISSUE ADHERENT COMPOSITIONS AND METHODS OF USE

(75) Inventors: Amarpreet S. Sawhney, Lexington, MA (US); Peter G. Edelman, Franklin, MA (US)

(73) Assignee: Incept LLC, Lexington, MA (US)

( * ) Notice: Subject to any disclaimer, the term of this patent is extended or adjusted under 35 U.S.C. 154(b) by 0 days.

(21) Appl. No.: 09/776,120

(22) Filed: Feb. 2, 2001

(65) Prior Publication Data

US 2002/0106409 A1 Aug. 8, 2002

(51) Int. Cl.[7] .................................................. A61K 9/14
(52) U.S. Cl. ........................ 424/489; 424/490; 424/491; 424/493; 424/497; 424/422; 424/423; 424/426
(58) Field of Search .................................. 424/422, 423, 424/426, 484, 486, 487, 488, 489, 490, 491, 493, 497, 499, 501, 400

(56) References Cited

U.S. PATENT DOCUMENTS

| | | | |
|---|---|---|---|
| 4,268,495 A | 5/1981 | Muxfeldt et al. ............... 424/1 |
| 4,456,711 A | 6/1984 | Pietsch et al. ............... 523/206 |
| 4,490,497 A | 12/1984 | Evrard et al. ............... 524/349 |
| 4,804,691 A | 2/1989 | English et al. ............... 523/118 |
| 5,122,614 A | 6/1992 | Zalipsky ....................... 548/520 |
| 5,410,016 A | 4/1995 | Hubbell et al. .............. 528/354 |
| 5,468,811 A | 11/1995 | Moro et al. ................... 525/263 |
| 5,527,856 A | 6/1996 | Rhee et al. .................. 525/54.1 |
| 5,614,204 A | 3/1997 | Cochrum ...................... 424/423 |
| 5,733,950 A | 3/1998 | Dunn et al. .................. 523/173 |
| 5,752,974 A | 5/1998 | Rhee et al. ................... 606/214 |
| 5,770,229 A | 6/1998 | Tanihara et al. ............. 424/488 |
| 5,874,500 A | 2/1999 | Rhee et al. .................. 525/54.1 |
| 6,312,725 B1 * | 11/2001 | Wallace et al. .............. 424/484 |

* cited by examiner

Primary Examiner—Thurman K. Page
Assistant Examiner—Liliana Di Nola-Baron
(74) Attorney, Agent, or Firm—Patterson, Thuente, Skaar & Christensen, P.A.

(57) ABSTRACT

Compositions and methods are provided for forming tissue-adherent hydrogels using substantially dry precursors. The dehydrated precursors are premixed prior to in situ therapy and utilize naturally-occurring body fluids as an aqueous environment that initiates transformation, which causes dissolution and nearly simultaneous crosslinking of the precursors, thus forming an insoluble hydrogel implant. The dehydrated precursor-based hydrogels may be used as sealants for fluid leaks from tissue, as adherent drug delivery depots, as means for augmenting and/or supporting tissue, and as means for serving a variety of other useful medical and surgical purposes.

34 Claims, 1 Drawing Sheet

DEHYDRATED HYDROGEL PRECURSOR-BASED, TISSUE ADHERENT COMPOSITIONS AND METHODS OF USE

FIELD OF THE INVENTION

This invention relates to hydrogels used as sealants for tissue fluid leaks, as adherent drug delivery depots, as means for augmenting and/or supporting tissue, and as means for serving a useful medical or surgical purpose. More particularly, the present invention relates to compositions and methods for forming tissue adherent hydrogels using substantially dry precursors.

BACKGROUND OF THE INVENTION

In situ therapy has primarily focused on transformation of precursor solutions into solids within a patient's body. Transformations have been achieved by a variety of means, including precipitation, polymerization, crosslinking, and desolvation. Precursor materials may be natural or synthetic, or a combination thereof. Examples of solution-based in situ therapy techniques include U.S. Pat. Nos. 4,804,691; 5,122,614; 5,410,16; 4,268,495; 5,527,856; 5,614,204; 5,733,950; and 5,874,500.

Significant limitations exist when using solutions for in situ therapy. Solutions of low viscosity may flow away and be cleared from an application site before transformation and solidification occurs. Furthermore, formulation of the solutions may be complex, as preparation of precursor solutions typically requires reconstitution of the precursors, or, when the solutions are stored frozen, thawing.

Polymerizable powdered mixtures have been combined with liquid initiators to form settable pastes for use as bone cements, as discussed in U.S. Pat. Nos. 4,456,711; 5,468,811; and 4,490,497. However, all these compositions and related methods for making medically-useful products from such compositions are limited by use of a non-aqueous solvent or initiator. Polymerizations are not activated by the presence of aqueous physiological surroundings.

A variety of applications exist for in situ therapy. During surgery, for example, tissues and organs may be damaged or traumatized, and may thereby develop leaks. Furthermore, the organs may be too fragile to manipulate and repair using conventional surgical means, such as suturing. In situations where leaks appear or where conventional surgical management is difficult, surgical adhesives and sealants may be useful.

Several tissue sealants are known in the art. The most commonly used biologically-based sealant is fibrin glue or fibrin sealant. This sealant typically comprises aqueous solutions of purified fibrinogen and thrombin. A coagulum is formed by mixing these two solutions together, and the coagulum may serve as a sealant or tissue adhesive. However, adhesion strength is limited, and setup time may be long. Furthermore, a wound leaking fluids is likely to wash the sealant away from an application site prior to solidification of the coagulum, thereby limiting the efficacy of fibrin glue. Likewise, the efficacy of all liquid sealants is limited by adherence of liquid sealants to tissue surfaces that present liquid interfaces. It therefore becomes important to have substantially dry surfaces prior to application of liquid tissue sealants. However, creation of dry application sites in situ is often unfeasible during surgery.

A product under the brand name Tachocomb (Behringwerke, Germany) has recently been introduced, which uses dry components to form a hemostatic patch of the fibrin sealant. The patch has been formed using horse collagen, bovine thrombin, and human fibrinogen. Since the component materials are procured from animal sources, allergic responses and disease transmission may result. The materials are also expensive to manufacture. Furthermore, the efficacy of fibrin-based sealants may be adversely affected by anticoagulants routinely administered as part of surgical and interventional procedures.

More recently, synthetic alternatives to fibrin sealants have been developed. One such material comprises photo-activated poly(ethylene glycol) ("PEG"), which is marketed as FocalSeal™ (Focal, Inc., Lexington, Mass.). Focal, Inc., claims that FocalSeal™ provides superior strength characteristics over fibrin sealants and glues. However, use of light to initiate polymerization limits applicability in surgical environments where bleeding is not effectively controlled, since blood impedes light transmission. Other surgical sealants, including synthetic sealants such as Co-Seal™, are marketed by Cohesion Technologies (Palo Alto, Calif.). However, these sealants, as well as FocalSeal™, require a dry surface for application.

In view of the drawbacks associated with previously-known methods and apparatus for in situ therapy, it would be desirable to provide methods and apparatus that overcome these drawbacks.

It further would be desirable to provide methods and apparatus that use dry materials procured from sources other than non-human animals.

It still further would be desirable to provide methods and apparatus for in situ therapy that are activated solely by the presence of aqueous physiological surroundings.

It further would be desirable to provide methods and apparatus that do not require complex formulation prior to use.

It would also be desirable to provide methods and apparatus that remain effective in the presence of anticoagulants.

It would be desirable to provide methods and apparatus for in situ therapy that are inexpensive to manufacture and are highly effective in clinical practice.

SUMMARY OF THE INVENTION

In view of the foregoing, it is an object of the present invention to provide methods and apparatus for in situ therapy that overcome drawbacks associated with previously-known methods and apparatus.

It is also an object of the present invention to provide methods and apparatus that use dry materials procured from sources other than non-human animals.

It is another object to provide methods and apparatus for in situ therapy that are activated solely by the presence of aqueous physiological surroundings.

It is yet another object to provide methods and apparatus that do not require complex formulation prior to use.

It still further is an object of the present invention to provide methods and apparatus that remain effective in the presence of anticoagulants.

It is an object of the present invention to provide methods and apparatus for in situ therapy that are inexpensive to manufacture and are highly effective in clinical practice or field use, such as a battle field where rapid medical attention may be needed.

These and other objects of the present invention are accomplished by providing compositions and methods for forming tissue-adherent hydrogels using substantially dry precursors. The dehydrated hydrogel precursors are pre-mixed prior to in situ therapy and utilize naturally-occurring body fluids as an aqueous environment that initiates transformation. The precursors do not form an insoluble, crosslinked solid until such time as they are exposed to the aqueous physiological setting. Upon exposure to the aqueous setting, dissolution and nearly simultaneous crosslinking of the dehydrated precursors occurs, thus forming an insoluble hydrogel implant. The implant is preferably bioabsorbable.

The dehydrated precursor-based hydrogels of the present invention may be used for a variety of medical applications, including use as sealants for fluid leaks from tissue, as adherent drug delivery depots, and as means for augmenting and/or supporting tissue. The hydrogels are typically a mixture of two or more individual dry precursors. The precursors may be selected for specific therapeutic uses, for example, adherence, coagulation of blood, dessication, etc. The precursors may be administered directly to an open wound site or may be dispensed using a means of application. The means of application may include, for example, a non-adhesive backing material, an absorbable backing material, a syringe applicator, a powder atomization or aerosolization system, or a needle-less injector.

When used as a sealant and applied to a wound site, rapid uptake of blood or other tissue fluid occurs, thereby facilitating crosslinking of the dehydrated precursor components and providing adherence of the resulting coagulum to underlying tissue. Additionally, active agents may be added to the precursors to further promote the sealing process. A high concentration of these active agents may be provided at a wound site.

The dry precursors of the present invention may also be delivered to target organs, such as a patient's lungs, by atomization of a finely micronized mixture. Contact with tissue fluids results in crosslinking and coating of mucosal tissues, thus providing an efficient means for drug delivery.

Exemplary compositions and methods of use in accordance with the present invention are provided hereinbelow.

BRIEF DESCRIPTION OF THE DRAWINGS

The above and other objects and advantages of the present invention will be apparent upon consideration of the following detailed description, taken in conjunction with the accompanying drawings, in which.

DETAILED DESCRIPTION OF THE INVENTION

Figure 1:
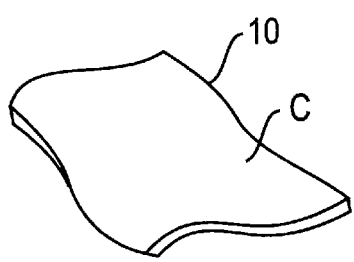
FIG. 1 is an isometric view of non-adhesive backing materials for use as a delivery system for sealants of the present invention.

The present invention provides medical sealant compositions that are in a substantially dry form. The compositions typically comprise a mixture of two or more individual dehydrated precursors, which activate upon exposure to fluid in a physiological environment. Upon exposure, dissolution and nearly simultaneous crosslinking of a composition's dehydrated precursors occurs, thus forming an insoluble hydrogel implant, which is preferably biodegradable. The hydrogels of the present invention may be used for a wide variety of medical applications, including use as sealants for fluid leaks from tissue, as adherent drug delivery depots, and as means for augmenting and/or supporting tissue. They may be administered directly to an open wound site or may be dispensed using a means of application, for example, a non-adhesive backing material, an absorbable backing material, a syringe applicator, a powder atomization or aerosolization system, or a needle-less injector, each of which is described in greater detail hereinbelow.

In a first embodiment, the precursors used for in situ gelation may comprise a lyophilized, or freeze-dried form, wherein lyophilization has been conducted on aqueous or organic solvents. Lyophilization advantageously provides very high surface area powders. Individual lyophilized precursors may then be compounded together or may be layered on top of each other, for example, in a corrugated sheet fashion. Corrugated structure is expected to advantageously promote interlocking of precursor layers. The layers may comprise components that interact with each other to form a crosslinked matrix. The crosslinks themselves may be physical or chemical in nature, or both.

As an example, a two-part dehydrated hydrogel precursor mixture may consist of an electrophilic, multifunctional poly(ethylene glycol) ("PEG") precursor and a multifunctional, nucleophilic PEG precursor. These two dehydrated components may be compounded together when dry. Upon exposure to an aqueous environment, rapid chemical crosslinking occurs and forms a hydrogel that is adherent to tissue.

As another example, a fully-synthetic, solid PEG particulate hydrogel composition may be provided that has application, for example, in hemostasis and/or space-filling procedures. A degradable PEG hydrogel is fabricated, then dried or lyophilized. The lyophilized hydrogel is pulverized to a particulate size configured for use with a given delivery system and treatment space.

The particulate composition may be fabricated as follows: first, the degradable hydrogel is made and pulverized by methods known to those of skill in the art, for example, by the methods described in Example 6 hereinbelow. The hydrogel is then treated to provide synthetic organic functional groups on its surface that either directly react with blood proteins or that are derivatized with other functional groups that react with proteins present in blood. For example, the hydrogel may be treated to provide an abundance of carboxylate groups on its surface. These carboxylate groups may be coupled using dicyclohexylcarbodiimide with groups such as N-hydroxysuccinimide ("NHS"). The particulate composition with NHS surface derivatization may then be prepared and packaged in an appropriate manner, such as lyophilization.

In use, the composition may be applied into a body space to form a degradable hydrogel. Upon hydration with water in blood, the lyophilized hydrogel swells, thereby partially or completely filling the space. In surface treatment applications, the surface of the space is more contiguously covered. The surface groups, once hydrated, become activated and react with blood proteins, resulting in a layer or filled space that is biocompatible, bioresorbable, and achieves hemostasis.

Free radical polymerization of lyophilized precursors may further facilitate chemical crosslinking by providing ethylenically unsaturated and substantially water soluble molecules containing necessary chemical initiators in dehydrated form. For example, polyalkylene oxide-based (meth) acrylated precursors may be used with redox initiators, such as t-butyl hydroperoxide and ferrous gluconate, dispersed within the polymeric mix. Upon contact with moisture, the co-initiating system is activated to produce free radicals that initiate crosslinking of the multiacrylated precursor to form a final implant. Several other water soluble macromers and initiating systems may be useful for this invention and will be apparent to those of skill in the art of polymer chemistry. In addition to free radical polymerization, mechanisms for chemical crosslinking include condensation polymerization, anionic or cationic polymerization, and step growth polymerization.

Similarly, physical crosslinking may be utilized with lyophilized precursors. Mechanisms for physical crosslinking include ionic interactions, hydrophobic interactions, hydrogen bonding, Van der Waals forces, and desolvation. For example, a composition consisting of an alginate precursor mixed with a calcium chloride precursor forms ionic crosslinks in the presence of an aqueous environment.

In an alternative embodiment in accordance with the present invention, the precursors may be formed using spray drying to form granules of pre-determined and controlled size. These granules optionally may be coated with a water dispersible or water soluble binding agent. The binding agent may comprise any of a number of water soluble or water dispersible, low melting point (preferably between 37–50° C.) substances. The binding agent is expected to help maintain a pre-defined configuration, such as a sheet or a cone or larger composite granules, by, for example, stacking the coated precursors in a desired configuration and then performing a brief treatment step, such as heating, to stabilize the desired configuration. This secondary processing step is expected to provide shapes of sealant devices tailored for specific surgical settings. For example, a conical shape may facilitate penetration of wounds, a sheet shape may be useful in abrasion-type lesions, etc.

Structures and additives that enhance fluid uptake into the dehydrated hydrogel precursors advantageously may be used in accordance with the principles of the present invention. For example, introduction of macroporosity into the structure of a shaped article formed from dehydrated precursors is expected to enable a rapid uptake of a fluid, such as blood. Rapid uptake facilitates drying in a surgical field and thus creates a good substrate for adherence. It also enables more rapid fusion of the precursors to form the hydrogel. Additives that enhance osmolarity of the hydrogel precursors can also be used to further enhance uptake of aqueous fluids. The additives may, for example, include salts, mannitol, sucrose, or other sugars. Substances that are naturally occurring within the body are preferred.

Referring now to FIG. 1, non-adhesive backing materials 10 optionally may be used with both the lyophilized and the spray dried sealants of the present invention. Backing materials 10 are preferably non-absorbable in nature to allow convenient application of dehydrated sealants to tissue, so as to prevent, for example, the surgeon's glove from becoming adherent to the sealant patch. Materials such as polytetrafluoroethylene, polyethylene, polyurethane, and silastic, among others, are expected to be useful for this purpose. Additional non-adhesive backing substrates may include silicone treated substrates. Also, coatings C optionally may be applied to backing materials 10 to help release the adhesive sealants from the backing materials, as well as to enhance the non-adhesive nature of the sheets. Potential coating materials include, for example, low molecular weight PEG (<2000 Da), which has a waxy consistency; glycerol; fatty acids; and sugars.

In another alternative embodiment, a coating of dehydrated hydrogel precursors may be formed. Where a first precursor is reactive with a second precursor during deployment of the device, a coating technique may be employed to deposit separable layers of the precursors. This may be achieved by proper selection of a solvent system and coating conditions such that, after deposition of a first layer of the first precursor, a second layer of the second precursor is deposited in such a manner as not to be reactive with the first precursor. In a still further alternative embodiment, the precursors may be provided in a solvent that is inert to interaction between the dry precursors.

Figure 2:
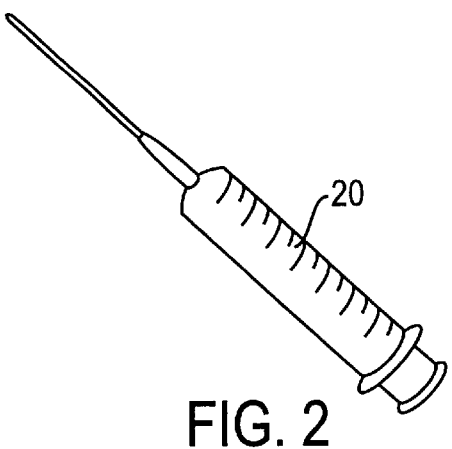
FIG. 2 is an isometric view of a syringe for use as a delivery system for the sealants of the present invention.
Figure 3:
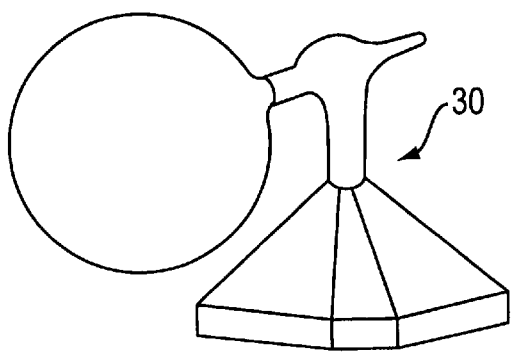
FIG. 3 is an isometric view of a powder atomizer delivery system.
Figure 4:
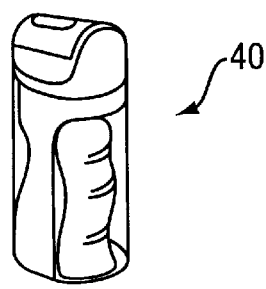
FIG. 4 is an isometric view of a previously known aerosolizing delivery system for use with the sealants of the present invention.
Figure 5:
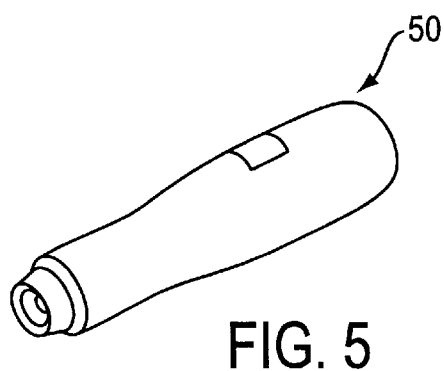
FIG. 5 is an isometric view of a previously known needle-less injector delivery system for use with the sealants.

The sealant compositions of dehydrated hydrogel precursors may be delivered using several delivery systems that are known in the medical and pharmaceutical art. For example, the hydrogels may be delivered using pre-filled syringe 20 of FIG. 2, or using gas powered powder atomizer 30 of FIG. 3, such as is used for delivering talcum powder in surgical applications. Other means for delivery are also envisioned, including aerosolizing apparatus, such as apparatus 40 of FIG. 4 that is being developed by Inhale Therapeutics or an alternative system being developed by the Aradigm Corp. Pneumatic, needle-less injectors, such as apparatus 50 of FIG. 5 marketed by Powderject Ltd. (U.K.), are also expected to facilitate delivery.

Figure 6:
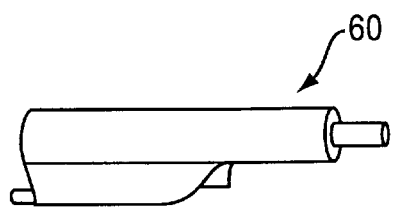
FIG. 6 is a side view of a previously known pneumatic injector delivery system.

Pneumatic injectors for delivering medications, especially fluent medications, without needles have been known for many years and are commercially available. For example, the Bioject Corporation (Portland, Oreg.) markets apparatus 60 of FIG. 6 under the trade name "Biojector 2000". Apparatus 60 allows needle-less injection of a wide range of fluent medications. More recently, pneumatic injection of powder-based compositions has been attempted, as illustrated by the Powderject system of apparatus 50 of FIG. 5.

Pneumatic injectors may be actuated by a variety of techniques, including injection of a compressed gas; such as argon, carbon dioxide, nitrogen, or helium; and spring actuation. The injectors may be partially or fully disposable, and often come packaged with a fill needle or vial adaptor to draw medication or an implant-forming material or solution from a vial into a syringe. The needle or vial adaptor is then discarded and the filled syringe is inserted into the device. A protective cap is present over the syringe to prevent touch contamination. In use, the syringe is inserted into the injector, the protective cap is removed, and the injector is firmly placed against a patient's skin at an orthogonal angle. The injector is actuated and contents of the syringe are delivered to the patient's tissue. Different syringe sizes provide different penetration depths within the tissue, including intradermal, subcutaneous, and intramuscular. In addition to a reduction in transmission risk of blood borne pathogens, needle-less injectors provide a wider distribution of treatment materials, as compared to standard hypodermic needles, which tend to deliver materials in a localized bolus. However, delivery of solutions still is hampered by rapid dissipation of the solutions from the site of administration.

In order to prolong the presence of treatment materials at the administration site, it is desirable to entrap the therapeutic entity or drug within an implant forming material. Thus, in situ implants formed using needle-less injectors are expected to provide prolonged presence at the administration site. This is expected to be useful in many applications, including genetic transfection, as well as delivery of transformed cells, naked DNA, liposomes, microparticles, cationic carriers complexed with DNA, viral vectors, and the like.

Further in accordance with the present invention, optional therapeutic agents may be added to the dehydrated sealants to create enhanced sealing efficacy or a locally adhesive depot for drug delivery. For example, incorporation of dehydrated human thrombin may lead to rapid coagulation of bleeding when delivered by an adhesive patch formed from the sealant compositions described above.

Additional wound healing capabilities may be imparted to these adhesive patches by incorporation of bioactive species. For example, anti-infective agents may be incorporated into patches used at abscess sites, bone growth factors may be incorporated into patches used at or near fracture sites, and angiogenic factors, such as VEGF and FGF, may be incorporated into patches used to stimulate blood vessel growth. Similarly, anti-angiogenic factors may be incorporated into patches applied at areas of tumor resection, to enable eradication of residual tumor cells from incomplete resection margins. Further therapeutic agents may include, for example, a wide variety of factors, proteins, peptides, oligonucleotides, genes, polysaccharides, proteoglycans, glycosaminoglycans, microparticles, and drugs, preferably of low molecular weight.

Advantageously, sealants of the present invention, created from dry precursors, may be provided as convenient single-pack kits, or as patches used as single units for each surgical defect. This is expected to decrease formulation time and provide more efficient utilization of materials, as compared to liquid surgical sealants.

In order to more fully describe various aspects of the present invention, a series of clinical examples are detailed below.

EXAMPLE 1

A dehydrated adhesive composition was formulated using two dehydrated hydrogel precursors. Precursor A consisted of 1 g poly(ethylene glycol) amine, and precursor B consisted of poly(ethylene glycol) extended with succinimidyl glutarate ester. The two precursors were mixed and ground together in a mortar and pestle until a smooth mixture was obtained. This mix was termed Mixture A. Mixture B was created like Mixture A, but with additional incorporation of 500 Units of human thrombin to the composition.

A midline laparotomy was created in a 100 lb. hog under general anesthesia. The hog was given 50 mg/Kg Heparin to induce anticoagulation. The hog's spleen was visualized. A scalpel was used to create a 2 cm long incision in 3 locations along the spleen. In the first location, 0.25 g of Mixture A was administered. In the second location, 0.25 g of Mixture B was administered. In the third location, no further treatment was administered. All three locations were compressed with gentle finger pressure and the time to hemostasis was noted. It was seen that hemostasis was obtained in Mixture A in 1 min, in Mixture B in 30 sec, and no hemostasis was obtained in the third location in 5 min.

EXAMPLE 2

The materials described in Example 1 were used in a rat liver resection model. A midline laparotomy was created in a rat and its liver was visualized. A 1 cm longitudinal section was removed from each of three liver lobes. 0.1 g of Mixture A and Mixture B were applied to the first and second resections, respectively. The third site was left untreated. Time to hemostasis was noted. No further pressure was applied to the sites. The first site ceased bleeding in 45 seconds, the second site in 15 seconds, and the third site was still seen to be bleeding after a period of 3 min.

EXAMPLE 3

A mixture of dehydrated precursors as described in Example 1 (e.g., Mixture A) may be spray coated with N-vinyl caprolactam, which is in a melted state at 37° C. The coated precursors may then be placed over a sheet of polyurethane backing material and smoothed out to form a 1 mm thick precursor layer. This layer of precursor briefly may be placed in an oven at 37° C. to fuse the precursors such that individual particles stick together, but the composition retains an open porous structure. This dehydrated composite and the backing sheet may be cut to a desired size for convenient application. An additional layer or packing housing may optionally be placed around the composition to prevent damage during storage and shipping.

EXAMPLE 4

A craniotomy was created in a dog in the temporal region. The dura was exposed and a scalpel was used to create a 1 cm long dural defect, with the help of a dural hook used to lift the dura. A gush of CSF was visually apparent as the arachnoid layer was cleaved. The durotomy was sutured shut using 8-0 Prolene suture. A valsalva maneuver that increases thoracic pressure to 40 cm of water was used to demonstrate a continued leak of CSF from the dura. A dehydrated hydrogel precursor composite sheet as described in Example 3 was cut into a 2 cm×1 cm size and placed over the dural defect. Gentle pressure was applied over the non-adhesive backing for about 30 sec. The seeping CSF was absorbed by the precursor composite and resulted in formation of a contiguous and tissue adherent hydrogel patch that sealed the CSF leak.

EXAMPLE 5

10 g of PEG-Succinimidyl glutarate (M.W. 10,000 Da) may be mixed with 400 mg of dilysine dihydrochloride, and the mixture may be ground overnight in a ball mill. The mixture may then be sieved to separate fine particles of less than 50 microns in size. These particles may be placed in a powder atomizer cylindrical container having a volume of about 1 liter. At one end of the atomizer is a mouth piece, and at the other end is an assembly that provides rapid injection of a burst of pressurized air in such a fashion that a dry mixture placed in the cylinder may be atomized and dispersed in the cylindrical chamber. Using the mouthpiece, the atomized precursor may be inhaled.

About 500 mg of the dehydrated mix may be combined with 200 mg of bovine insulin to create a free flowing mix. This insulin-containing dehydrated mixture may be introduced in the cylindrical chamber described above, dispersed with the air injection, and inhaled by a diabetic patient. Upon contacting mucosal surfaces of the patient's bronchioles, the mixture is expected to briefly dissolve and polymerize to form a thin hydrogel layer that entraps insulin and allows a slow delivery of the drug over time. More efficient utilization and dosing of the drug with fewer side effects is expected. Furthermore, it is expected that a range of drugs including, for example, growth factors, genetic matter, and painkillers may be easily delivered in this fashion.

EXAMPLE 6

10 g of a PEG-succinimidyl glutarate ("SG-PEG") precursor, having a molecular weight of 20,849 Da, may be reacted with 193 mg of a trilysine precursor. The SG-PEG precursor may be reconstituted in pH 4 phosphate, while the trilysine precursor may be reconstituted in pH 8 borate buffer. The precursors are mixed and are applied as a coating to a skived teflon sheet, using a draw down blade. The coated sheet is put into a constant humidity chamber, such that the coating is allowed to react and gel overnight at room temperature. During this time, aminolysis is completed, and amide bonds between amines of the trilysine precursor and terminal carboxylate groups of the SG-PEG precursor are formed. Some hydrolysis of the formed gel may also occur at ester linkages on the PEG side of the glutarate, resulting in free acid groups that are covalently attached to the gel. The concentration of these acid groups may be controlled by controlling hydrolysis time, temperature, and pH, as is known in the art.

The hydrogel film may next be lyophilized to remove all water. The resultant dry, solid film may be pulverized to an appropriate particulate size. A slurry of the crosslinked, insoluble particulate hydrogel may then be prepared in an anhydrous organic solvent to which dicyclohexylcarbodiimide ("DCC") is added, followed by N-hydroxysuccinimide (NHS). The insoluble particles have thus been derivatized with NHS groups. These are then dried, packaged, and sterilized in a manner appropriate with intended final use. Since the NHS may be coupled to the previously-free acid groups, dicyclohexylurea ("DCU") may form, which is subsequently removed by repeated solvent extraction steps.

Adhesive sealants and drug delivery systems as described in this invention provide a new modality of efficacious and economical sealants. Pulmonary delivery of such dehydrated hydrogel precursors mixed with therapeutic compounds is expected to be an efficient and non-invasive way of administering in situ therapy and controlled drug delivery.

Although particular embodiments of the present invention have been described above in detail, it will be understood that this description is merely for purposes of illustration. Further variations will be apparent to one skilled in the art in light of this disclosure and are intended to fall within the scope of the appended claims.

What is claimed is:

1. A hydrogel system for in situ therapy comprising an applicator associated with at least two substantially dry hydrogel precursors for delivery to a common location, the dry hydrogel precursors being water soluble and having functional groups for forming chemical crosslinks with each other at physiological pH to form a hydrogel in situ upon exposure to an aqueous fluid from a physiological environment.

2. The hydrogel system of claim 1, wherein the dry hydrogel precursors upon exposure to an aqueous physiological environment further form crosslinks that are physical in nature, the physical crosslinks being formed by a mechanism selected from the group consisting of ionic interactions, hydrophobic interactions, hydrogen bonding, Van der Waals forces and desolvation.

3. The hydrogel system of claim 1, wherein the functional groups form chemical crosslinks by a mechanism selected from the group consisting of free radical polymerization, condensation polymerization, anionic or cationic polymerization and step growth polymerization.

4. The hydrogel system of claim 1, wherein the chemical crosslinks are both chemical and physical in nature.

5. The hydrogel system of claim 1, wherein the substantially dry hydrogel precursors comprise a form chosen from the group consisting of lyophilized, spray dried, or in a solvent that is inert to interaction between the dry precursors.

6. The hydrogel system of claim 1, wherein the substantially dry hydrogel precursors are compounded together prior to exposure to the fluid from the physiological environment.

7. The hydrogel system of claim 5, wherein the substantially dry hydrogel precursors in lyophilized form comprise a corrugated structure.

8. The hydrogel system of claim 5, wherein the substantially dry hydrogel precursors in spray dried form comprise granules of controlled size.

9. The hydrogel system of claim 8, wherein the granules comprise a coating of a binding agent that helps create a shaped article configuration.

10. The hydrogel system of claim 9, wherein the hydrogel comprises a configuration chosen from the group consisting of a sheet, a cone, and a composite granule.

11. The hydrogel system of claim 1, wherein the hydrogel precursors are adapted to form a hydrogel that is biodegradable.

12. The hydrogel system of claim 1 wherein the applicator is chosen from the group consisting of a non-adhesive backing material, an absorbable backing material, a syringe applicator, a powder atomization system, and a needle-less injector.

13. The hydrogel system of claim 12, wherein the non-adhesive backing material is non-absorbable.

14. The hydrogel system of claim 13, wherein the non-adhesive backing material is fabricated from a material chosen from the group consisting of polytetrafluoroethylene, polyethylene, polyurethane, and silastic.

15. The hydrogel system of claim 12, wherein the non-adhesive backing material further comprises a coating, the coating configured to facilitate release of the hydrogel from the non-adhesive backing material.

16. The hydrogel system of claim 15, wherein the coating is fabricated from a material chosen from the group consisting of poly(ethylene glycol) with a molecular weight less than 2000 Da, glycerol, fatty acid, and sugar.

17. The hydrogel system of claim 1 further comprising therapeutic agents in communication with the hydrogel precursors.

18. The hydrogel system of claim 17, wherein the therapeutic agents are chosen from the group consisting of thrombin, anti-infective agents, bone growth factors, angiogenic factors, anti-angiogenic factors, growth factors, proteins, peptides, oligonucleotides, genes, polysaccharides, proteoglycans, microparticles, glycosaminoglycans, and drugs.

19. The hydrogel system of claim 1 wherein the hydrogel system is provided in a form chosen from the group consisting of a kit and a patch.

20. A method of forming a dehydrated precursor-based water-insoluble hydrogel medical implant in situ comprising:

providing at least two substantially dry hydrogel precursors that are water soluble and include functional groups that make chemical crosslinks to each other to form the water-insoluble hydrogel medical implant when mixed together in an aqueous environment at physiological PH;

delivering the hydrogel precursors to an implantation site in situ in a patient; and exposing the precursors to aqueous physiological fluids at physiological pH at the implantation site.

21. The method of claim 20, wherein providing a hydrogel precursor comprises providing a hydrogel precursor associated with a bioactive species.

22. The method of claim 20 further comprising using the hydrogel medical implant for delivering drugs.

23. The method of claim 20, wherein forming the medical implant seals fluid leaks from the implantation site.

24. The method of claim 20, wherein forming the medical implant supports or augments the implantation site.

25. The method of claim 20, wherein delivering the hydrogel precursors to the implantation site comprises inhaling the hydrogel precursors.

26. A method of forming hydrogel particulates comprising:

providing a hydrogel;

removing water from the hydrogel;

pulverizing the hydrogel to particulates of controlled size; and treating the particulates to provide synthetic organic functional groups on a surface of the particulates, the functional groups configured to form chemical crosslinks with tissue and/or blood components.

27. The method of claim 26 further comprising lyophilizing the particulates.

28. The method of claim 26, wherein providing synthetic organic functional groups comprises providing electrophilic groups on at least a portion of the particulates.

29. The method of claim 28 wherein providing the electrophilic groups comprises a step of providing N-hydroxysuccinimide groups.

30. The method of claim 26 further comprising applying the particulates into a body space, thereby forming a bioreactive, degradable hydrogel in situ.

31. The method of claim 30, wherein forming a bioreactive, degradable hydrogel in situ comprises:

hydrating the particulates, thereby causing the particulates to swell and partially or completely fill the body space; and reacting the particulates with tissue and/or blood components to form the biocompatible, degradable hydrogel.

32. The hydrogel system of claim 1, wherein the functional groups include an electrophile and a nucleophile.

33. The hydrogel system of claim 32 wherein at least one of the hydrogel precursors comprises poly(ethylene) glycol and the electrophile or the nucleophile.

34. The hydrogel system of claim 1, wherein the dry precursors are powders.

* * * * *

UNITED STATES PATENT AND TRADEMARK OFFICE
CERTIFICATE OF CORRECTION

PATENT NO. : 6,703,047 B2
DATED : March 9, 2004
INVENTOR(S) : Amarpreet S. Sawhney and Peter G. Edelman It is certified that error appears in the above-identified patent and that said Letters Patent is hereby corrected as shown below:

Column 10,
Line 60, please delete "PH" and insert -- pH --

Signed and Sealed this

Twenty-first Day of June, 2005

JON W. DUDAS
*Director of the United States Patent and Trademark Office*